(12) United States Patent
Bureiko et al.

(10) Patent No.: US 8,034,127 B2
(45) Date of Patent: Oct. 11, 2011

(54) THICKENED HAIR COLOURANT AND BLEACHING COMPOSITIONS

(75) Inventors: Andrei Sergeevich Bureiko, Sunningdale (GB); Juergen Schmenger, Weiterstadt (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/884,940

(22) Filed: Sep. 17, 2010

(65) Prior Publication Data

US 2011/0067723 A1 Mar. 24, 2011

(30) Foreign Application Priority Data

Sep. 18, 2009 (EP) .................................... 09170757

(51) Int. Cl.
*A61Q 5/10* (2006.01)
(52) U.S. Cl. ............. 8/405; 8/431; 8/435; 8/552; 8/554; 8/633; 8/637.1; 8/107; 8/111
(58) Field of Classification Search .............. 8/405, 431, 8/435, 552, 554, 633, 637.1, 107, 111
See application file for complete search history.

(56) References Cited

U.S. PATENT DOCUMENTS

| | | | |
|---|---|---|---|
| 5,622,666 A | 4/1997 | Struszczyk et al. | |
| 5,716,418 A | 2/1998 | Matzik et al. | |
| 5,736,498 A | 4/1998 | Gray | |
| 6,117,915 A | 9/2000 | Pereira et al. | |
| 7,179,302 B2 | 2/2007 | Boswell | |
| 7,186,275 B2 | 3/2007 | Boswell et al. | |
| 7,431,740 B2 | 10/2008 | Cottard et al. | |
| 7,597,720 B2 | 10/2009 | Marsh | |
| 7,875,269 B2 | 1/2011 | Bureiko | |
| 7,887,600 B2 | 2/2011 | Bureiko et al. | |
| 2001/0002254 A1 | 5/2001 | Duffer | |
| 2003/0226217 A1 | 12/2003 | Bowes | |
| 2004/0237218 A1 | 12/2004 | Marsh et al. | |
| 2006/0117498 A1 | 6/2006 | Bureiko et al. | |
| 2007/0000070 A1 | 1/2007 | Vena | |
| 2007/0209124 A1 | 9/2007 | Bureiko et al. | |
| 2008/0010754 A1* | 1/2008 | Bureiko et al. | .................. 8/406 |
| 2008/0120791 A1 | 5/2008 | Hoffmann | |
| 2009/0119852 A1 | 5/2009 | Marsh | |
| 2011/0067722 A1 | 3/2011 | Bureiko et al. | |

FOREIGN PATENT DOCUMENTS

| | | |
|---|---|---|
| DE | 102006034956 A1 | 5/2007 |
| EP | 1762220 A2 | 3/2007 |

OTHER PUBLICATIONS

Kirk-Othmer, "Encyclopedia of Chemical Technology," Third Ed., 1982, vol. 3, pp. 896-900.
Kirk-Othmer, "Encyclopedia of Chemical Technology," Third Ed., 1982, vol. 15, pp. 439-458.
MacGregor, E.A., et al., "Polymers in Nature," John Wiley & Son, Ch. 6, pp. 240-328, 1980.
Martell, A.E., et al., "Critical Stability Constants," vol. 1, Plenum Press, New York & London (1974).
Martell, A.E., et al., "Metal Complexes in Aqueous Solution," Plenum Press, New York & London (1996).
Sagarin, "Cosmetic Science and Technology," Interscience, Special Ed., vol. 2, pp. 308-310. (1972).
Whistler, Roy L., Editor, "Industrial Gums—Polysaccharides and their Derivatives," Academic Press, Inc. (1992).
U.S. Appl. No. 12/986,698, filed Jan. 1, 2011, Bureiko, et al.

* cited by examiner

*Primary Examiner* — Eisa B Elhilo
(74) *Attorney, Agent, or Firm* — Laura R. Grunzinger

(57) ABSTRACT

The present invention relates to hair coloring and hair bleaching compositions comprising at least one oxidizing agent, a specified gel network thickener system comprising a specified tertiary system, a cationic polymer and a mica and or titanium oxide. The compositions surprisingly provide improved hair colorant and bleaching compositions which deliver lift, lightening and color, whilst minimizing damage which are easy to manufacture and which improve adhesion of the composition to the hair roots.

13 Claims, No Drawings

US 8,034,127 B2

THICKENED HAIR COLOURANT AND BLEACHING COMPOSITIONS

FIELD OF THE INVENTION

The present invention relates to hair colour and hair bleaching compositions.

BACKGROUND OF THE INVENTION

The permanent alteration of the colour of keratinous fibres, in particular human hair, by the application of hair dyes is well known. In order to provide the consumer with the hair colour and the intensity of colour desired, a very complex chemical process is utilized. Permanent hair dyeing formulations typically comprise oxidative hair dye precursors, which can diffuse into the hair through the cuticle and into the cortex where they can then react with each other and suitable oxidising agents to form the end dye molecules. Due to the larger size of these resultant molecules they are unable to readily diffuse out of the hair during subsequent washing with water and/or detergents; hence delivering a consumer-desired permanency of colour. This reaction typically takes place in an aggressive environment at approximately pH 10 in the presence of an alkalizing agent and in the presence of an oxidizing agent. Moreover, the consumer repeats this process regularly in order to maintain the desired hair colour and shade and the intensity of colour and to ensure continual, even coverage of the hair including coverage of new hair growth.

The manufacturer of such products is also required to work within a large number of constraints. Since these products are being placed in direct contact with the consumers' skin, the potential exists for accidental contact with the eye or for ingestion (for example), which can occur during the dyeing process. Therefore, the formulation must meet rigorous safety requirements and not induce any allergic reactions. In addition to meeting these requirements, the products must also be optically and olfactory pleasing to the consumer. In particular, the products also need to meet certain physical parameters in order to ensure that the product can be easily applied to the hair by the consumer to provide the desired effect, without unintentional staining of the consumers' clothes, skin particularly along the hair line or other objects.

The manufacturer is also required to provide the hair colouring consumer a large range of different resulting colours. Some consumers may just wish to enhance the natural colour of the hair, whilst others may wish to cover grey or completely alter the hair colour to a different natural appearing hair colour or a 'synthetic' appearing hair colour. Consequently, the manufacturer may provide over twenty different formulations, of varying colours and shades, to address the range of consumer specific needs. These formulations have to be individually formulated and are typically complex formulae containing a mixture of different dye compounds. As a result the manufacture of such product ranges can be costly and complex.

However, despite the fact that commercial hair dyeing products have been available for many years, the products still exhibit a number of consumer-related deficiencies.

Typically permanent hair dye products will contain an alkali, typically a source of ammonia. This serves the purpose of swelling the hair allowing the entry of the dye precursor molecules into the hair and also improves the lightening effect of the oxidising agent, which is typically hydrogen peroxide. However, ammonia is also volatile and its associated odour is extremely unpleasant to the consumers' of such products, particularly as these hair dye products are used in close proximity to the nasal region. Hence, it would be highly desirable to provide an oxidative hair colouring and/or bleaching composition, which delivers the consumer required lightening level and colour, but which has reduced or eliminated the detectable ammonia odour.

In fact another deficiency area in current hair colouring products is the provision of hair colouring products which deliver the required hair lightening effect. Delivering the required level of lightening is particularly important in order to provide the full range of colour shades demanded by the consumer, especially for blonde shades and grey coverage. Such products pose particular difficulties to the manufacturer, as they usually require the use of high levels of oxidising agent and ammonia in order to deliver the required lightening effect. However, in additional to the problems associated with the presence of high levels of ammonia in these products, as discussed herein above, the presence of these high levels of ammonia and/or oxidizing agent also affect the condition of the hair and may in some cases induce mild skin irritation on the scalp. In particular, the hydrophilicity of the hair surface is increased during the colouring process, which alters the sensory perception of the hair and its overall manageability during, immediately after colouring and during the subsequent wash and styling cycles until the next colourant application. Hence, it would also be highly desirable to provide an oxidative hair colouring and/or bleaching composition which delivers the required lightening and/or colour without unnecessary hair damage.

Moreover, in order to provide a product which the consumer can easily apply to the hair without dripping onto the skin, clothes or bathroom or salon surfaces, hair colourant products must be designed such that the applied composition has a certain required viscosity. This is either achieved by providing the dye composition and the oxidizing composition as so called thin-thin type liquid formulations which are thickened upon mixing, or, where at least one of the components, either the dye composition or the oxidizing composition, preferably the dye composition, is provided as a thickened formulation which thickens the total composition upon mixing. These thickened compositions can be achieved by the use of a gel network systems which provide the desired thickness to either the dye composition or the oxidizing composition or, preferably both compositions. Furthermore, such gel networks are highly desirable as they also provide additional benefits of a cream like texture, conditioner like feel and appearance, smooth rinse and improved hair feel. Such thickened gel network systems are described in WO2007/102119, EP1878469 and EP1878469. These compositions have a viscosity range typical for retail applications which is in the range of 1 Pas to 8 Pas.

In the professional hair salon market, the hair colour professionals typically do not use predetermined combinations of dye and oxidizing compositions or kits as in the retail market. Instead, the hair salon professionals are able to use any combination of commercially available dye and oxidizing compositions. For the professional market, the available oxidizing compositions are typically provided with a variety of viscosities. Consequently, the dye compositions that are combined with the oxidizing compositions need to be formulated to ensure that they are able to thicken the oxidizing compositions to the required viscosity independent of the viscosity of the starting composition of the oxidizing agent.

In addition, in the professional salon the mixed dye and oxidative compositions are typically much thicker than the mixed compositions provided for the retail market and are typically in the range of 9 Pas to 16 Pas. This is to enable the hair salon professionals to use a variety of techniques to apply the composition in order to provide their clients with the desired results. Typically this is delivered using the brush and bowl technique. Compositions which have a viscosity typical to retail applications are considered not acceptable by hair colour professionals.

However, certain professional thickened compositions comprising such gel network systems have been found to exhibit a phenomenon whereby after application to the hair, the composition tends to crack away from the root along the length of the hair strand away from the root. As a result the roots do not necessarily receive the required amount of composition in order to deliver the desired result. Particularly for regular hair colourant users, virgin hair growth coverage at the roots is essential for a satisfactory outcome and this problem needs to be addressed, without the necessity for the hair salon professional to continuously check and reapply the composition to the roots to ensure complete coverage. This problem of lack of effective root adhesion is further exacerbated with compositions comprising hydrogen peroxide and carbonate oxidizing systems.

Hence it would be desirable to provide the consumer, particularly the hair salon professional with a hair colorant product, which in addition to delivering the required lightening, colour deposition, has the required rheology and viscosity such that it can be utilised by hair salon professionals and which does not exhibit any cracking away from the roots during or after application of the composition on the hair.

It has now been surprisingly found that oxidative hair colouring compositions comprising at least one oxidizing agent, a specified gel network thickener system comprising a specified tertiary system, and a cationic polymer and a mica or titanium oxide as defined herein having the required viscosity and ionic strength so it can be used to achieve variety of professional hair colour applications while exhibiting excellent hair root adhesion.

SUMMARY OF THE INVENTION

The present invention relates to a hair colouring and hair bleaching composition comprising an oxidizing agent, a gel network thickening system comprising
i) a first anionic surfactant component selected from C14 to 30 alkyl phosphate, C14 to C30 alkyl ether phosphate or mixtures thereof,
ii) a second component selected from C14 to C30 fatty alcohols and
iii) a third non-ionic surfactant component selected from polyoxyethylene C14 to C30 alkyl ethers, wherein said composition comprises at least 1% of said first surfactant component and at least 3% of the sum of said first surfactant component, second component and third surfactant component and wherein said composition further comprises at least 0.2% of a mica, or titanium oxide and or mixtures thereof and at least 0.2% of a cationic polymer and wherein said composition has an ionic strength of less than 0.75 mole/kg and a viscosity of from 9 Pas to 16 Pas.

In another embodiment, the present invention relates to a method of treating hair comprising the steps of applying the composition of the present invention to the hair for from about 2 to 60 minutes and subsequently rinsing said composition from the hair.

In another embodiment the present invention relates to the use of the composition of the present invention to improve the adhesion of the composition to the hair preferably the hair roots.

DETAILED DESCRIPTION OF THE INVENTION

While the specification concludes with claims, which particularly point out and distinctly claim the invention, it is believed the present invention will be better understood from the following description.

As used herein the term "hair" to be treated may be "living" i.e. on a living body or may be "non-living" i.e. in a wig, hairpiece or other aggregation of non-living keratinous fibres. Mammalian, preferably human hair is preferred. However wool, fur and other keratin containing fibres are suitable substrates for the compositions according to the present invention.

All percentages are by weight of the total composition unless specifically stated otherwise. When more than one composition are used during a treatment, the total weight to be considered is the total weight of all the compositions applied on the hair simultaneously (i.e. the weight found "on head") unless otherwise specified. All ratios are weight ratios unless specifically stated otherwise. All molar concentrations are by weight of the total composition and presented as number of moles of component(s) in one kilogram of the composition, or "mole/kg". When more than one composition are used during a treatment, the total weight to be considered is the total weight of all the compositions applied on the hair simultaneously (i.e. the weight found "on head") unless otherwise specified.

Oxidizing Agent

The compositions according to the present invention comprise or are used in combination with a composition that comprises at least one source of an oxidizing agent. Preferred oxidizing agents for use herein are water-soluble peroxygen oxidizing agents. "Water-soluble" as defined herein means that in standard condition at least 0.1 g, preferably 1 g, more preferably 10 g of said oxidizing agent can be dissolved in 1 liter of deionized water. The oxidizing agents are valuable for the initial solubilisation and decolorisation of the melanin (bleaching) and accelerate the oxidation of the oxidative dye precursors (oxidative dyeing) in the hair shaft.

Any oxidizing agent known in the art may be utilized in the present invention. Preferred water-soluble oxidizing agents are inorganic peroxygen materials capable of yielding hydrogen peroxide in an aqueous solution. Water-soluble peroxygen oxidizing agents are well known in the art and include hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulphates and the like. These inorganic perhydrate salts may be incorporated as monohydrates, tetrahydrates etc. Alkyl and aryl peroxides, and or peroxidases may also be used. Mixtures of two or more such oxidizing agents can be used if desired. The oxidizing agents may be provided in aqueous solution or as a powder which is dissolved prior to use. Preferred for use in the compositions according to the present invention are hydrogen peroxide, percarbonate (which may be used to provide a source of both oxidizing agent and carbonate ions and or ammonium ions), persulphates and combinations thereof.

According to the present invention the compositions comprise from about 0.1% to about 10% by weight, preferably from about 1% to about 7% by weight, and most preferably from about 2% to about 5% by weight of an oxidizing agent.

Gel Network Thickener

According to the present invention, the hair colouring and bleaching compositions comprise a gel network thickener system. The gel network thickener system of this invention is typically provided in the dye composition and subsequently mixed with the oxidizing composition. The gel network thickener system of this invention is defined as a thickening system comprising a tertiary component system. This system comprises first anionic surfactant component selected from C14 to C30 alkyl phosphate, C14 to C30 alkyl ether phosphate and or mixtures thereof, a second component selected from C14 to C30 fatty alcohols and a third non-ionic surfactant component selected from polyoxyethylene C14 to C30 alkyl ethers.

Those skilled in the art will recognize that gel network thickener systems usually have a complex structure of networked lamellar bi-layers and/or vesicles and sometimes crystals. These systems usually have creamy appearance and feel and are thus particularly desirable.

In particular the gel network system of the present invention allows for easy and efficient mixing of the dye composition with the oxidizing composition containing a source of hydrogen peroxide. Furthermore, the gel network system delivers the desired mixed viscosity level, independent of the developer composition per se and its viscosity prior to mixing. The latter property is of particular benefit for example in professional hair colour applications in hair salons, where enabling the flexibility to utilize a range of different developer compositions and or viscosity is often particularly desirable.

Without being bound by theory, it is believed that gel network thickener system described in this invention have appropriate geometrical arrangement in the gel network lamellar bi-layers, preventing bi-layers from de-swelling and thus resisting viscosity loss. It is further believed that non-ionic surfactant of this invention has more suppressed swelling due to the higher ionic strength in the dye composition, and thus stability is provided by the ionic surfactant, whereas after dilution with the oxidizing composition, the concentration of ions is reduced leading to non-ionic surfactant re-swelling to provide the required additional thickening.

The first anionic surfactant component of the gel network thickener system is selected from C8 to C30, preferably C14 to 18 alkyl phosphate, C8 to C30 preferably C14 to C18 alkyl ether phosphate or mixtures thereof. Preferably the alkyl ether phosphates have an average 1 to 20, preferably 1 to 10 and most preferably 1 to 3 ethylene oxide units. According to the present invention the composition comprises at least about 1% by weight of said first surfactant component, preferably from about 1% to 3%, more preferably from about 1.2% to 2% by weight of the composition of said first surfactant component. The first surfactant component assists in the formation of the gel network and is preferably utilized at the above levels to assist the maintenance of the desired rheology range particularly at the upper value to prevent excessive stickiness.

According to the present invention, the gel network system of the present invention comprises as a second component, a linear or branched C14 to C30 fatty alcohols. Most preferably the second component is selected from cetyl, stearyl, cetostearyl or behenyl alcohols or mixtures thereof. According to the present invention the composition may comprise from about 2% to 8%, preferably from about 4% to 6% of said fatty alcohol by weight of said composition. Typically, the second component may be comprised within the dye composition or the oxidizing composition or both, preferably the second component is comprised in both compositions. The second component assists in the stabilization of the gel network system and also assists in the maintenance of the desired rheology range particularly at the upper value to prevent excessive stickiness.

The third surfactant component of the gel network thickener system is a non-ionic surfactant, selected from polyoxyethylene C14 to C30 alkyl ethers, comprising one or more polyethyleneoxide chains, preferably having at least about 25, preferably from about 50 to 200, most preferably from about 100 to 200 ethylene oxide units. Suitable surfactants include steareth-25, steareth-100, steareth-150, steareth-200 and mixtures thereof. The third surfactant component acts as a co emulsifier and stabilizer of the gel network system. Moreover, whilst not being bound by theory the third surfactant assists in the formation of a soft and smooth composition. According to the present invention the composition may comprise from about 0.1% to 5%, preferably from about 0.5% to 1% of said third surfactant component by weight of said composition.

More than one surfactant and or component of each of the above specified types of the surfactants or components can be used in the gel network of the present invention. The compositions of the present invention comprise a total amount of said first surfactant component, said second component and said third surfactant component of at least about 3%, preferably at least about 4%, more preferably at least about 5% by weight of the composition.

Cationic Polymer

Cationic polymers suitable for use herein can be chosen from those comprising units of at least one amine group chosen from primary, secondary, tertiary and quaternary amine groups that may either form part of the main polymer chain or be borne by a side substituent that is directly attached to the main polymer chain. Such cationic polymers generally have a number average molecular mass ranging from about 500 to about $5 \times 10^6$, or more preferably from about 1000 to about $3 \times 10^6$. Preferably the cationic polymers are selected from polymers of the polyamine, polyamino amide and polyquaternary ammonium type.

Polymers of the polyamine, polyamino amide and polyquaternary ammonium type that may be used include but are not limited to:

1) Homopolymers and copolymers derived from acrylic or methacrylic esters or amides. Copolymers of these polymers can also comprise at least one unit derived from comonomers which may be chosen from the family of acrylamides, methacrylamides, diacetone acylamides, acrylamides and methacrylicamides substituted on the nitrogen with at least one group chosen from lower (C1-C4) alkyls, acrylic and methacrylic acids and esters thereof, vinyllactams such as vinylpyrrolidone and vinylcaprolactam, and vinyl esters.

Copolymers of acrylamide and of methacryloyloxyethyltrimethylammonium methosulfate, examples of which include polymers known via the INCI nomenclature as Polquaternium-5, such as the products sold under the names Reten 210, Reten 220, Reten 230, Reten 240, Reten 1104, Reten 1105, Reten 1006 by the company Hercules and Merquat 5, Merquat 5 SF by the company Nalco.

Copolymers of vinylpyrrolidone and dimethylaminopropyl methacrylamide, examples of which include polymers known via the INCI nomenclature as Polyquaternium-28, such as the products sold under the name Gafquat HS-100 by the company International Speciality Products (ISP). Copolymers of vinyl pyrrolidone and dialkyaminoalkyl acrylates or methacrylates, examples of which include polymers known via the INCI nomenclature as Polquaternium-11, such as the products sold under the name Gafquat 440, Gafquat 734, Gafquat 755, Gafquat 755N by the company International Speciality Products (ISP), and Luviquat PQ11 PM by the company BASF and Polyquat-11 SL by the company Sino Lion.

Copolymers vinylpyrrolidone, dimethylaminopropyl methacrylamide and methacryloylaminopropyl lauryldimonium chloride, examples of which include polymers known via the INCI nomenclature as polyquaternium-55, such as the products sold under the name Styleze W-20 by the company International Speciality Products (ISP).

Copolymers of acrylic acid, acrylamide and methacrylamidopropyltrimonium chloride, examples of which include polymers known via the INCI nomenclature as Polyquaternium-53, such as the products sold under the name Merquat 2003 by the company Nalco.

Copolymers of dimethyaminopropylacrylate (DMAPA), acrylic acid and acrylonitrogens and diethyl sulfate, examples of which include polymers known via the INCI nomenclature as Polyquaternium-31, such as the products sold under the name Hypan QT100 by the company Lipo.

Copolymers of acrylamide, acrylamidopropyltrimonium chloride, 2-amidopropylacrylamide sulfonate, and dimethyaminopropylacrylate (DMAPA), examples of which include polymers known via the INCI nomenclature as polyquaternium-43, such as the products sold under the name Bozequat 4000 by the company Clairant.

Copolymers of acrylic acid, methylacrylate and methacrylamidopropyltrimonium chloride, examples of which include polymers known via the INCI nomenclature as Polyquaternium-47, such as the products sold under the name Merquat 2001 and Merquat 2001N sold commercially by Nalco.

Copolymers of methacryloyl ethyl betaine, 2-hydroxyethyl methacrylate and methacryloyl ethyl trimethyl ammonium chloride, examples of which include polymers known via the INCI nomenclature as Polyquaternium-48, such as the products sold under the name Plascize L-450 by the company Goo Chemical.

Copolymers of acrylic acid diallyl dimethyl ammonium chloride and acrylamide, examples of which include polymers known via the INCI nomenclature as polyquaternium 39, such as the products sold under the name Merquat 3330 and Merquat 3331 by the company Nalco.

Further examples include copolymers of methacrylamide methacrylamido-propyltrimonium and methacryloylethyltrimethyl ammonium chloride and their derivatives, either homo or copolymerised with other monomers, examples of which include polymers known via the INCI nomenclature as: Polyquaternium-8, Polyquaternium-9, Polyquaternium-12, Polyquaternium-13 Polyquaternium-14, Polyquaternium-15, such as the products sold under the name Rohagit KF 720 F by the company Rohm, Polyquaternium-30, such as the products sold under the name Mexomere PX by the company Chimex, Polyquaternium-33, Polyquaternium-35, Polyquaternium-36, such as the products sold under the name Plex 3074 L by the company Rhon, Polyquaternium 45, such as the products sold under the name Plex 3073L by the company Rohn, Polyquaternium 49, such as the products sold under the name Plascize L-440 by the company Goo Chemicals, Polyquaternium 50 such as the products sold under the name Plascize L-441 by the company Goo Chemicals, Polyquaternium-52.

2) Cationic polysaccharides, such as cationic celluloses and cationic galactomannan gums. Among the cationic polysaccharides that maybe mentioned, for example, are cellulose ether derivatives comprising quaternary ammonium groups and cationic cellulose copolymers or cellulose derivatives grafted with a water-soluble quaternary ammonium monomer and cationic galactomannan gums. Examples include but are not limited to Copolymers of hydroxyethylcelluloses and diallyldimethyl ammonium chlorides, examples of which include polymers known via the INCI nomenclature as Polyquaternium-4, such as the products sold under the name Celquat L 200 and Celquat H 100 by the company National Starch. Copolymers of hydroxyethylcelluloses and a trimethyl ammonium substituted epoxide, examples of which include polymers known via the INCI nomenclature as Polyquaternium-10, such as the products sold under the name AEC Polyquaternium-10 by the company A&E Connock, Catinal C-100 Catinal HC-35 Catinal HC-100 Catinal HC-200 Catinal LC-100 Catinal LC-200 by the company Toho, Celquat SC-240C Celquat SC-230M, by the company National Starch, Dekaquat 400, Dekaquat 3000 by the company Dekker, Leogard GP by the company Akzo Nobel, RITA Polyquta 400 RITA, Polyquta 3000 by the company RITA, UCARE Polymer JR-125 UCARE Polymer JR-400 UCARE Polymer JR-30M UCARE Polymer LK UCARE Polymer LR 400 UCARE Polymer LR 30M by the company Amerchol.

Copolymers of hydroxyethylcelluloses and lauryl dimethyl ammonium substituted epoxides, examples of which include polymers known via the INCI nomenclature as Polyquaternium-24, such as the products sold under the name Quatrisoft polymer LM-200 by the company Amerchol. Derivatives of Hydroxypropyl Guar, examples of which include polymers known via the INCI nomenclature as Guar Hydroxypropyltrimonium Chloride, such as the products sold under the name Catinal CG-100, Catinal CG-200 by the company Toho, Cosmedia Guar C-261N, Cosmedia Guar C-261N, Cosmedia Guar C-261N by the company Cognis, DiaGum P 5070 by the company Freedom Chemical Diamalt, N-Hance Cationic Guar by the company Hercules/Aqualon, Hi-Care 1000, Jaguar C-17, Jaguar C-2000, Jaguar C-13S, Jaguar C-14S, Jaguar Excel by the company Rhodia, Kiprogum CW, Kiprogum NGK by the company Nippon Starch.

Hydroxypropyl derivatives of Guar Hydroxypropyltrimonium Chloride, examples of which include polymers known via the INCI nomenclature as Hydroxypropyl Guar Hydroxypropyltrimonium Chloride, such as the products sold under the name Jagaur C-162 by the company Rhodia.

3) Polyamino amide derivatives resulting from the condensation of polyalkylene polyamines with polycarboxylic acids followed by alkylation with difunctional agents. Among the derivative, mention may be made for example to adipic acid/dimethylaminohydroxypropyl/diethylenetriamine.

4) Polymers obtained by reaction of a polyalkylene polyamine comprising two primary amines groups and at last one secondary amine group with a decarboxylic acid chosen from diglycolic acids and saturated aliphatic dicarboxylic acids comprising from 3 to 8 carbon atoms. Non-limiting examples of such derivatives include the adipic acid/epoxypropyl/diethylenetriamine.

5) Cyclopolymers of dialkdiallylamine or of dialkyldiallyammonium, among which polymers mention may be made of:

Dimethyldiallyammonium chloride polymers, examples of which include polymers known via the INCI nomenclature as Polyquaternium-6, such as the products sold under the name Merquat 100 by the company Nalco, Mirapol 100 by the company Rhodia, Rheocare CC6 by the company Cosmetic Rheologies, AEC polyquaternium-6 by the company A&E Connock, Agequat 400 by the company CPS, Conditioner P6 by the company 3V Inc., Flocare C106 by the company SNF, Genamin PDAC by the company Clariant, Mackernium 006 by the company McIntyre.

Copolymers of acrylamides and dimethyldiallylammonium chlorides monomers, examples of which include polymers known via the INCI nomenclature as Polyquaternium-7, such as the products sold under the name AEC Polyquaternium-7 by the company A&E Connock, Agequat-5008, Agequat C-505 by the company CPS, Conditioner P7 by the company 3V Inc. Flocare C 107 by the company SNF Mackernium 007, Mackernium 007S by the company McIntyre, ME Polymer 09W by the company Toho, Merquat 550, Merquat 2200, Merquat S by the company Nalco, Mirapol 550 by the company Rhodia, Rheocare CC7, Rheocare CCP7 by the company Cosmetic Rheologies, Salcare HSP-7, Salcare SC10, Salcare Super 7 by the company Ciba.

Copolymers of dimethyldiallylammoniumchlorides and acrylic acids, examples of which include polymers known via the INCI nomenclature as polyquaternary-22, such as the products sold under the name Merquat 280 and Merquat 295 by the company Nalco.

6) Quaternary diammonium polymers comprising repeat units corresponding to [—N+(R1)(R2)-A1-N+(R3)(R4)-B1-][2X—], in which R1, R2, R3 and R4, which may be identical or different, are chosen from aliphatic, alicyclic and arylaliphatic radicals comprising from 1 to 20 carbon atoms and from lower hydroxyalkylaliphatic radicals, or R1, R2, R3 and R4, together or separately, constitute, with the nitrogen atoms to which they are attached, heterocycles optionally comprising a second heteroatom other then nitrogen, or R1, R2, R3 and R4, are chosen from liner or branched C1-C6 alkyl radicals substituted with at least one group chosen from nitrile, ester, acyl and amide groups and groups of —CO—O—R5-D and —CO—NH—R5-D wherein R5 is chosen from alkylene groups and D is chosen from quaternary ammonium groups. A1 and B1, which may be identical or different, are chosen from linear and branched, saturated or unsaturated polymethylene groups comprising 2 to 20 carbon atoms. The polymethylene groups may comprise, linked to or intercalated in the main ring, at least one entity chosen from aromatic rings, oxygen and sulphur atoms and sulphoxide, sulphone, disulphide, amino, alkylamino, hydroxyl, quaternary, ammonium, ureido, amide and ester groups, and X— is an anion derived from inorganic and organic acids. D is chosen from a glycol residue, a bis-secondary diamine residue, a bis-primary diamine residue or a ureylene group. An examples of which include polymers known via the INCI nomenclature as Hexadimethrine chloride, where R1, R2, R3 and R4 are each methyl radicals, A1 is (CH2)$_3$ and B1 is (CH2)6 and X═Cl. Further examples of which include polymers known via the INCI nomenclature as polyquaternium-34 where R1 and R2 are ethyl radicals and R3 and R4 are methyl radicals and A1 is (CH2)3 and B1 is (CH2)3 and X═Br, such as the products sold under the name Mexomere PAX by the company Chimax.

7) Polyquaternary ammonium polymers comprising repeating units of formula [—N+(R6)(R7)-(CH2)r-NH—CO—(CH2)q-(CO)t-NH—(CH2)s-N+(R8)(R9)-A-][2X—], in which R6, R7, R8 and R9 which may be identical or different, are chosen from a hydrogen atom and a methyl, ethyl, propyl, hydroxyethyl, hydroxypropyl, and —CH2CH2(OCH2CH2) pOH radicals, wherein p is equal to 0 or an integer ranging from 1 to 6, wherein R6, R7, R8 and R9 do not all simultaneously represent a hydrogen atom. R and s which maybe identical or different are each an integer ranging from 1 to 6, q is equal to 0 or an integer ranging from 1 to 34 and X— is anion such as a halide. T is an integer chosen to be equal to 0 or 1. A is chosen from divalent radicals such as —CH2-CH2-O—CH2-CH2. Examples of which include Polymers known via the INCI nomenclature as polyquaternium-2, where r═s═3, q═0, t═0, R6, R7, R8 and R9 are methyl groups, and A is —CH2-CH2-O—CH2-CH2, such as the products sold under the name Ethpol PQ-2 from Ethox and Mirapol A-15 by the company Rhodia.

Polymers known via the INCI nomenclature as polyquaternium-17 where r═s═3, q═4, t═1 R6, R7, R8 and R9 are methyl groups, and A is —CH2-CH2-O—CH2-CH2.

Polymers known via the INCI nomenclature as Polyquaternium 18, where r═s═3, q═7, t═1 R6, R7, R8 and R9 are methyl groups, and A is —CH2-CH2-O—CH2-CH2

Polymers known via the INCI nomenclature as the block copolymer formed by the reaction of Polyquaternium-2 with Polyquaternium-17, known as Polyquaternium 27, such as the products sold under the name Mirapol 175 by the company Rhodia.

8) Copolymers of vinylpyrrolidones and of vinylimidazoles and optionally vinylcaprolactums, examples of which include polymers known via the INCI nomenclature as Polyquaternary-16 formed from methylvinylimidazolium chlorides and vinylpyrrolidones, such as the products sold under the name Luviquat FC370, Luviquat FC550, Luviquat FC905, Luviquat HM-552 by the company BASF. Or copolymers of vinylcaprolactams and vinylpyrrolidones with methylvinylimidazolium methosulfates, examples of which include polymers known via the INCI nomenclature as Polyquaternium-46, such as the products sold under the name Luviquat Hold by the company BASF. Or copolymers of vinylpyrrolidones and quaternized imidazolines, examples of which include polymers known via the INCI nomenclature polyquaternary 44, such as the products sold under the name Luviquat Care by the company BASF 9) Polyamines such as the product Polyquart H sold by Cognis under the reference name polyethylene glycol (15) tallow polyamine in the CTFA dictionary.

10) Cross linked methacryloyloxy(C1-C4)alkyltri(C1-C4)alkylammonium salt polymers such as the polymers obtained by homopolymerisation of dimethylaminoethyl methacrylates quaternized with methyl chloride, or by copolymerisation of acrylamides with dimethylaminoethyl methacrylates quaternized with methyl chloride, the homo or copolymerisation being followed by crosslinking with a compound comprising olefinic unsaturation, such as methylenebisacrylamides, examples of which include polymers known via the INCI nomenclature as Polyquaternium-37, such as the products sold under the name Synthalen, CN Synthalen CR, Synthalen CU, sold by 3V sigma, or as a dispersion in another media such as the products sold under the name Salcare SC95 and Salcare SC96 by the company Ciba or Rheocare CTH(E) by the company Cosmetic Rheologies. Or in another example of which include polymers known via the INCI nomenclature as Polyquaternium-32, or when sold as a dispersion in mineral oil such as the products sold under the name Salcare SC92 by the company Ciba.

11) Further examples of cationic polymers include polymers known via the INCI nomenclature as Polyquaternium 51, such as the products sold under the name Lipidure-PMB by the company NOF, via the INCI nomenclature as Polyquaternium 54, such as the products sold under the name Qualty-Hy by the company Mitsui, via the INCI nomenclature as Polyquaternium 56 such as the products sold under the name Hairrol UC-4 by the company Sanyo chemicals, and via the INCI nomenclature as Polyquaternium 87 such as the product sold under the name of Luviquat sensation by the company BASF.

12) Silicone polymers comprising cationic groups and/or groups which may be ionised into cationic groups. For example: cationic silicones of the general formula (R10-N+(CH3)2)-R11-(Si(CH3)2-O)x-R11-(N+(CH3)2)-R10), where R10 is an alkyl derived from coconut oil, and R11 is (CH2CHOCH2O(CH2)3 and x is a number between 20 and 2000, examples of which include polymers known by the INCI nomenclature as Quaternium 80, such as the products sold under the name as Abil Quat 3272 and Abil Quat 3474 sold commercially by Goldschmidt. Silicones containing groups which may be ionised into cationic groups, for example aminosilicones containing at least 10 repeating siloxane —(Si(CH3)2-O) units within the polymer chain, with either terminal, graft or a mixture of terminal and graft aminofunctional groups. Example functional groups are not limited to aminoethylaminopropyl, aminoethylaminoisobutly, aminopropyl. In the case of graft polymers, the terminal siloxane units can either be (CH3)3Si—O or R12 (CH3)2Si—O, where R12 can be either OH or OR13, where R13 is a C1-C8 alky group, or a mixture of both functional terminal groups. These silicones are also available as pre-formed emulsions. Polymer with terminal siloxane units of (CH3)3Si—O examples of which include polymers known by the INCI nomenclature as trimethylsilylamodimethicone, such as the products sold under the name as DC-2-8566, DC 7224 and DC-2-8220 sold commercially by Dow Corning and SF1708 and SM 2125 sold commercially by GE Silicones and Wacker Belsil ADM 653 sold commercially by Wacker silicones. Further examples include polymers with terminal siloxane units of (R12O)(CH3)2Si—O where R12 can be either OH or OR13, where R13 is a C1-C8 alky group, or a mixture of both functional terminal groups, known by the INCI nomenclature as amodimethicone, such as the products sold under the name as Wacker Belsil ADM 1100, Wacker Belsil ADM 1600, Wacker Belsil ADM 652, Wacker Belsil ADM 6057E, Wacker Belsil ADM 8020 sold commercial by Wacker Silicones, DC929, DC939 and DC949 sold commercially by Dow Corning and SM2059 sold commercially by GE silicones. Silicones containing groups which may be ionised into cationic groups—for example silicones containing at least 10 repeating siloxane —(Si(CH3)2-O) units within the polymer chain, with either terminal, graft or a mixture of terminal and graft aminofunctional groups, together with additional functional groups. Additional functional groups can include polyoxyalkylene, the reaction product of amines and carbinols, alky chains. For example products know by the INCI nomenclature as methoxy PEG/PPG-7/3 Aminopropyl Dimethicone, such as the product sold under the name of Abil Soft AF100 sold commercially by Degussa. For example products know by the INCI nomenclature as Bis(C13-15 Alkoxy) PG Amodimethicone, such as the product sold under the name of DC 8500 sold commercially by Dow Corning.

Preferred cationic polymers for use herein are polyquaternium 37, polyquaternium 7, polyquaternium 22, polyquaternium 87 and mixtures thereof. Particularly preferred are polyquaternium 37 and polyquaternium 22 and mixtures thereof. The compositions of the present invention comprises at least about 0.2%, preferably from about 0.5% to 2% by weight of the composition of a cationic polymer.

Mica/Titanium Dioxide

Among the uncoated titanium oxides suitable for use herein, the following products may be mentioned in particular:
As powders: BAYERTITAN and DIOXYDE DE TITANE A provided by the company BAYER; 70110 CARDRE UF TIO2 provided by the company CARDRE;
As a 10%, 20% or 30% aqueous dispersion and with a particle size of 15, 20 or 60 nanometers; SUNVEIL 1010, 1020, 1030, 2020, 2030, 6010, 6030 provided by the company CATALYSTS & CHEMICALS; MICRO TITANIUM DIOXIDE-USP GRADE provided by the company COLOR TECHNIQUES.

Among the coated titanium oxides suitable for use herein, the following products may be mentioned in particular;
Coated with polydimenthylsiloxane (CARDRE ULTRAFINE TITANIUM DIOXIDE AS provided by the company CARDRE);
Coated with polymethylhydrogenosiloxane (untreated titanium oxide coated with polymethylhydrogenosiloxane sold under the trade name Cosmetic White SA-C47-051-10 by the company MYOSHI); those coated with perfluoronpolymethyl isopropyl ether (CARDRE MICA FHC 70173 OR 70170 CARDRE UF TIO2 FHC provided by the company CARDRE); those coated with silica (SPHERITITAN AB provided by the company CATALYSTS & CHEMICALS;
Coated with teflon (CS-13997 TEFLON COATED TITANIUM DIOXIDE provided by the company CLARK COLORS); those coated with polyester (EXPERIMENTAL DESOTO BEADS provided by the company DESOTO);
Coated with chitosan (CT-2 TITANIUM DIOXIDE MT-500SA provided by the company DAINIHON KASEI);
Coated with N-lauroyl-L-lysine (LL-5 TITANIUM DIOXIDE A 100, or alternatively LL-3 TITANIUM DIOXIDE MT-100SA, or alternatively LL-5 TITANIUM DIOXIDE CR-50, or alternatively LL-5 TITANIUM DIOXIDE MT-100SA, or alternatively LL-5 TITANIUM DIOXIDE MT-500SA, provided by the company DAINIHON KASEI).

Among the mica-titaniums suitable for use herein, the following products may be mentioned in particular:
FLONAC FS 20 C, FLONAC ME 10 C, FLONAC MG 10 C, FLONAC M1 10 C, FLONAC ML 10 C, FLONAC MS 10 C, provided by the company ECKART; TIMICA IRIDESCENT RED, or alternatively MATTINA GREEN provided by the company ENGELHARD; MATTINA GREEN, or alternatively TIMIRON GREEN MP-165 (17212), or alternatively TIMIRON STARLUSTER MP-115 (17200), or alternatively TIMIRON SUPER SPARKLE MP-148 (17297), TIMIRON GLEAMER MP-45 provided by the company MERCK.

According to the present invention the compositions comprise at least from about 0.2%, preferably from about 0.5% to 1.5% by weight of the composition of mica and or titanium oxide and or mixtures thereof which may be coated or uncoated.

Whilst not being bound by theory it is believed that the cationic polymer and mica and or titanium oxide deliver an improved root adhesion profile by modifying the rheological behaviour of the composition whilst also altering the surface interaction between the composition and the hair to which it is applied.

Ionic Strength

According to the present invention the compositions have an ionic strength as defined herein of less than 0.75 mole/kg, preferably from 0.1 to less than 0.75 mole/kg, more preferably from 0.2 to 0.6 mole/kg. Whilst not being bound by theory, it is believed that the ionic strength value also affects the resultant viscosity and root adhesion properties of the composition. The ionic strength can be affected by salt resources such as the dyes, sodium sulphate, ammonium carbonate anti-oxidants and chelants such as EDDS. The dye tends to have the greatest effect on the ionic strength and thus the amounts added in order to provide any particular shade need to be considered in terms of ionic strength as well as dye outcome in order to prevent viscosity and root adhesion problems.

The ionic strength of the composition is a function of the concentration of all ions present in that solution and is determined according to the formula:

$$I = \frac{1}{2}\sum_{i=1}^{n} m_i z_i^2$$

where $m_i$=molality of ion i (M=mol·/Kg $H_2O$), $z_i$=charge number of that ion, and the sum is taken over all ions in the solution. For example, for a 1:1 electrolyte such as sodium chloride, the ionic strength is equal to the concentration, but for $MgSO_4$ the ionic strength is four times higher. Generally multivalent ions contribute strongly to the ionic strength.

For example the ionic strength of a mixed 0.050 M $Na_2SO_4$ and 0.020 M NaCl solution is: I=½((2×(+1)²×0.050)+(+1)²×0.020+(−2)²×0.050+(−1)²×0.020)=0.17 M.

Viscosity

According to the present invention the compositions have a viscosity of from 9 to 16 Pas, preferably from 9 to 15 Pas more preferably from 10 to 14 Pas and most preferably from 11 to 13 Pas. Viscosity is determined according to the test method defined hereinafter. This viscosity range allows the hair salon professionals to have maximum flexibly to utilize one of numerous application techniques that may be required by any particular client providing a composition which has conditioner like properties and which is not too thick and sticky.

Additional Components

The compositions of the present invention may further comprise additional ingredients which include, but are not limited to, hair dyeing agents such as oxidative dye precursors, non-oxidative pre-formed dyes, carbonate ion sources, additional thickeners and/or rheology modifiers, solvents, radical scavenger, enzymes, additional surfactants, conditioning agents, carriers, antioxidants, stabilizers, chelants, perming actives, perfume, reducing agents (thiolactic acid), hair swelling agents and/or polymers. Some of these additional components are detailed hereafter.

Alkalizing Agent

According to the present invention the composition may optionally comprises an alkalizing agent, preferably a source of ammonium ions and or ammonia. Particularly, preferred alkalizing agents are those which provide a source of ammonium ions. Any source of ammonium ions is suitable for use herein. Preferred sources include ammonium chloride, ammonium sulphate, ammonium nitrate, ammonium phosphate, ammonium acetate, ammonium carbonate, ammonium hydrogen carbonate, ammonium carbamate, ammonium hydroxide, ammonium percarbonate salts, ammonia and mixtures thereof. Particularly preferred are ammonium carbonate, ammonium carbamate, ammonia, ammonium hydroxide and mixtures thereof. The compositions of the present invention may comprise from about 0.1% to about 10% by weight, preferably from about 0.5% to about 5%, most preferably from about 1% to about 3% of an alkalizing agent, preferably ammonium ions. Preferably, if present, the ammonium ions and carbonate ions are present in the composition at a weight ratio of from 3:1 to 1:10, preferably 2:1 to 1:5.

Preferably, the compositions of the present invention have a pH of from about 12 to about 7.5, more preferably from about 11 to about 8.4 and most preferably from about 10 to about 8.5.

The pH of the compositions can be determined by using either a Mettler Toledo MP220 or a MP225 pH equipment, fitted with a standard laboratory pH electrode. The equipment is calibrated before each use using standard calibration buffers and using standard calibration procedure.

Hair Dyes

The hair compositions of the present invention are preferably hair colouring compositions which comprise oxidative dyeing compositions. Such compositions comprise oxidative hair dye precursors or developers (also known as primary intermediates) that will deliver a variety of hair colors to the hair. These small molecules are activated by the oxidizing agent and react with further molecules to form a larger colored complex in the hair shaft.

The precursors can be used alone or in combination with other precursors, and one or more can be used in combination with one or more couplers. Couplers (also known as color modifiers or secondary intermediates) are generally colorless molecules that can form colors in the presence of activated precursors, and are used with other precursors or couplers to generate specific color effects or to stabilize the color. The choice of precursors and couplers will be determined by the color, shade and intensity of coloration that is desired. The precursors and couplers can be used herein, singly or in combination, to provide dyes having a variety of shades ranging from ash blonde to black.

These compounds are well known in the art, and include aromatic diamines, aminophenols, aromaticdiols and their derivatives (a representative but not exhaustive list of oxidation dye precursor can be found in Sagarin, "Cosmetic Science and Technology", "Interscience, Special Edn. Vol. 2 pages 308 to 310). It is to be understood that the precursors detailed below are only by way of example and are not intended to limit the compositions and processes herein.

Developers

Suitable developers for use in the compositions described herein include, but are not limited to, p-phenylenediamine derivatives, e.g. benzene-1,4-diamine (commonly known as p-phenylenediamine); 2-chloro-benzene-1,4-diamine; N-phenyl-benzene-1,4-diamine; N-(2-ethoxyethyl)benzene-1,4-diamine; 2-[(4-amino-phenyl)-(2-hydroxy-ethyl)-amino]-ethanol (commonly known as N,N-bis(2-hydroxyethyl)-p-phenylenediamine); (2,5-diamino-phenyl)-methanol; 1-(2'-Hydroxyethyl)-2,5-diaminobenzene; 2-(2,5-diamino-phenyl)-ethanol; N-(4-aminophenyl)benzene-1,4-diamine; 2,6-dimethyl-benzene-1,4-diamine; 2-isopropyl-benzene-1,4-diamine; 1-[(4-aminophenyl)amino]-propan-2-ol; 2-propyl-benzene-1,4-diamine; 1,3-bis[(4-aminophenyl)(2-hydroxyethyl)amino]propan-2-ol; $N^4,N^4$,2-trimethylbenzene-1,4-diamine; 2-methoxy-benzene-1,4-diamine; 1-(2,5-diaminophenyl)ethane-1,2-diol; 2,3-dimethyl-benzene-1,4-diamine; N-(4-amino-3-hydroxy-phenyl)-acetamide; 2,6-diethylbenzene-1,4-diamine; 2,5-dimethylbenzene-1,4-diamine; 2-thien-2-ylbenzene-1,4-diamine; 2-thien-3-ylbenzene-1,4-diamine; 2-pyridin-3-ylbenzene-1,4-diamine; 1,1'-biphenyl-2,5-diamine; 2-(methoxymethyl)benzene-1,4-diamine; 2-(aminomethyl)benzene-1,4-diamine; 2-(2,5-diaminophenoxy)ethanol; N-[2-(2,5-diaminophenoxy)ethyl]-acetamide; N,N-dimethylbenzene-1,4-diamine; N,N-diethylbenzene-1,4-diamine; N,N-dipropylbenzene-1,4-diamine; 2-[(4-aminophenyl)(ethyl)amino]ethanol; 2-[(4-amino-3-methyl-phenyl)-(2-hydroxy-ethyl)-amino]-ethanol; N-(2-methoxyethyl)-benzene-1,4-diamine; 3-[(4-aminophenyl)amino]propan-1-ol; 3-[(4-aminophenyl)-amino]propane-1,2-diol; N-{4-[(4-aminophenyl)amino]butyl}benzene-1,4-diamine; 2-[2-(2-{2-[(2,5-diaminophenyl)-oxy]ethoxy}ethoxy)ethoxy] benzene-1,4-diamine; 1,3-bis(N(2-Hydroxyethyl)-N-(4-amino-phenyl)amino)-2-propanol; 2,2'-[1,2-Ethanediyl-bis-(oxy-2,1-ethanediyloxy)]-bis-benzene-1,4-diamine;

p-aminophenol derivatives such as: 4-amino-phenol (commonly known as p-aminophenol); 4-methylamino-phenol; 4-amino-3-methyl-phenol; 4-amino-2-hydroxymethyl-phenol; 4-amino-2-methyl-phenol; 4-amino-1-hydroxy-2-(2'-hydroxyethylaminomethyl)benzene; 4-amino-2-methoxymethyl-phenol; 5-amino-2-hydroxy-benzoic acid; 1-(5-amino-2-hydroxy-phenyl)-ethane-1,2-diol; 4-amino-2-(2-hydroxyethyl)-phenol; 4-amino-3-(hydroxymethyl)phenol; 4-amino-3-fluoro-phenol; 4-amino-2-(aminomethyl)-phenol; 4-amino-2-fluoro-phenol; 1-hydroxy-2,4-diaminobenzene; o-phenylenediamine derivatives such as: 3,4-Diaminobenzoic acid and salts thereof; o-aminophenol derivatives such as: 2-amino-phenol (commonly known as o-aminophenol); 2,4-diaminophenol; 2-amino-5-methyl-phenol; 2-amino-5-ethyl-phenol; 2-amino-6-methyl-phenol; N-(4-amino-3-hydroxy-phenyl)-acetamide; and 2-amino-4-methyl-phenol; and heterocyclic derivatives such as: pyrimidine-2,4,5,6-tetramine (commonly known as 2,4,5,6-tetraminopyrimidine); 1-methyl-1H-pyrazole-4,5-diamine; 2-(4,5-diamino-1H-pyrazol-1-yl)ethanol; $N^2,N^2$-dimethyl-pyridine-2,5-diamine; 2-[(3-amino-6-methoxypyridin-2-yl)amino]ethanol; 6-methoxy-$N^2$-methyl-pyridine-2,3-diamine; 2,5,6-triaminopyrimidin-4(1H)-one; pyridine-2,5-diamine; 1-isopropyl-1H-pyrazole-4,5-diamine; 1-(4-methylbenzyl)-1H-pyrazole-4,5-diamine; 1-(benzyl)-1H-pyrazole-4,5-diamine; 1-(4-chlorobenzyl)-1H-pyrazole-4,5-diamine; pyrazolo[1,5-a]pyrimidine-3,7-diamine; 5,6,7-trimethylpyrazolo[1,5-a]pyrimidin-3-ylamine hydrochloride; 7-methylpyrazolo[1,5-a]pyrimidin-3-ylamine hydrochloride; 2,5,6,7-teramethylpyrazolo[1,5-a]pyrimidin-3-ylamine hydrochloride; 5,7-di-tert-butylpyrazolo[1,5-a]pyrimidin-3-ylamine hydrochloride; 5,7-di-trifluoromethyl-pyrazolo[1,5-a]pyrimidin-3-ylamine hydrochloride; 2-methylpyrazolo[1,5-a]pyrimidin-3,7-diamine hydrochloride; 4-hydroxy-2,5,6-triaminopyrimidine; 1-hydroxyethyl-4,5-diaminopyrazole; 2,5-diaminophenylethyl alcohol; and salts thereof.

Additional developers are selected from the group consisting of N-(3-furylmethyl)benzene-1,4-diamine; N-thiophen-3-ylmethyl-benzene-1,4-diamine; N-(2-furylmethyl)benzene-1,4-diamine; N-thiophen-2-ylmethyl-benzene-1,4-diamine; 3-(2,5-diamino-phenyl)-N-ethyl-acrylamide; 2-[3-(3-amino-phenylamino)-propenyl]-benzene-1,4-diamine; 2-[3-(4-amino-phenylamino)-propenyl]-benzene-1,4-diamine; 2-(6-methyl-pyridin-2-yl)-benzene-1,4-diamine; 2-pyridin-2-yl-benzene-1,4-diamine; 2-[3-(4-amino-phenylamino)-propenyl]-benzene-1,4-diamine; 2-[3-(3-amino-phenylamino)-propenyl]-benzene-1,4-diamine; 3-(2,5-diamino-phenyl)-N-ethyl-acrylamide; 2-thiazol-2-yl-benzene-1,4-diamine; 4-hydroxy-benzoic acid (2,5-diamino-benzylidene)-hydrazide; 3'-fluoro-biphenyl-2,5-diamine; 2-propenyl-benzene-1,4-diamine; 2'-chloro-biphenyl-2,5-diamine; N-thiophen-3-ylmethyl-benzene-1,4-diamine; N-(3-furylmethyl)benzene-1,4-diamine; 4'-methoxy-biphenyl-2,5-diamine; N-(4-amino-benzyl)-benzene-1,4-diamine; 2-methyl-5-[(1-H-pyrrol-2-ylmethyl)-amino]-phenol; 5-[(furan-2-ylmethyl)-amino]-2-methyl-phenol; 5-isopropylamino-2-methyl-phenol; biphenyl-2,4,4'-triamine hydrochloride; 5-(4-amino-phenyl)aminomethyl-benzene-1,3-diamine hydrochloride; 5-phenylaminomethyl-benzene-1,3-diamine hydrochloride; 2-[4-amino-2-(3,5-diamino-benzylamino)-phenoxy]-ethanol hydrochloride; 5-(3-amino-phenyl)aminomethyl-benzene-1,3-diamine hydrochloride; N-(2-amino-benzyl)-benzene-1,3-diamine hydrochloride; N-furan-2-ylmethyl-benzene-1,3-diamine hydrochloride; 2-[(3-amino-phenylamino)-methyl]-phenol hydrochloride; 4-amino-2-propylaminomethyl-phenol; N-benzo[1,3]dioxol-5-ylmethyl-benzene-1,3-diamine hydrochloride; N-[4-amino-2-(2-hydroxy-ethyl)-2H-pyrazol-3-yl]-3-(5-amino-2-hydroxy-phenyl)-acrylamide; 4-amino-2-(isopropylamino-methyl)-phenol; 4-thiophen-3-yl-benzene-1,3-diamine; 5-phenylaminomethyl-benzene-1,3-diamine hydrochloride; 5-(3-amino-phenyl)aminomethyl-benzene-1,3-diamine hydrochloride; 4-thiophen-3-yl-benzene-1,3-diamine; 2',4'-diamino-biphenyl-4-ol; 5-cyclobutylamino-2-methyl-phenol; 5-cyclobutylamino-2-methyl-phenol; 4-amino-2-(pyridin-3-ylaminomethyl)-phenol; 5-(3-amino-phenyl)aminomethyl-benzene-1,3-diamine hydrochloride; 5-allylaminomethyl-benzene-1,3-diamine hydrochloride; N-(4-amino-benzyl)-benzene-1,3-diamine hydrochloride; N-benzyl-benzene-1,3-diamine hydrochloride; 3-[(3-amino-phenylamino)-methyl]-phenol hydrochloride; N-(4-methoxy-benzyl)-benzene-1,3-diamine hydrochloride; N-thiophen-2-ylmethyl-benzene-1,3-diamine hydrochloride; 4-Amino-2-[(2-hydroxy-5-nitro-phenylamino)-methyl]-phenol; 2',4'-diamino-biphenyl-4-ol hydrochloride; biphenyl-2,4,4'-triamine; 5-(4-amino-phenyl)aminomethyl-benzene-1,3-diamine hydrochloride; 2-[4-amino-2-(3,5-diamino-benzylamino)-phenoxy]-ethanol hydrochloride; 5-allylaminomethyl-benzene-1,3-diamine hydrochloride; 5-(3-amino-phenyl)aminomethyl-benzene-1,3-diamine hydrochloride; N-(4-amino-benzyl)-benzene-1,3-diamine hydrochloride; N-benzyl-benzene-1,3-diamine hydrochloride; 3-[(3-amino-phenylamino)-methyl]-phenol hydrochloride; N-(2-amino-benzyl)-benzene-1,3-diamine hydrochloride; N-(4-methoxy-benzyl)-benzene-1,3-diamine hydrochloride; N-furan-2-ylmethyl-benzene-1,3-diamine hydrochloride; 2-[(3-amino-phenylamino)-methyl]-phenol hydrochloride; N-thiophen-2-ylmethyl-benzene-1,3-diamine hydrochloride; N-benzo[1,3]dioxol-5-ylmethyl-benzene-1,3-diamine hydrochloride; N-[4-amino-2-(2-hydroxy-ethyl)-2H-pyrazol-3-yl]-3-(5-amino-2-hydroxy-phenyl)-acrylamide hydrochloride; 4-amino-2-propylaminomethyl-phenol; 4-amino-2-(isopropylamino-methyl)-phenol; 4-amino-2-[(2-hydroxy-5-nitro-phenylamino)-methyl]-phenol hydrochloride; 2-methyl-5-[(1-H-pyrrol-2-ylmethyl)-amino]-phenol; 5-[(furan-2-ylmethyl)-amino]-2-methyl-phenol; 5-isopropylamino-2-methyl-phenol; 5-cyclobutylamino-2-methyl-phenol; 4-amino-2-(pyridin-3-ylaminomethyl)-phenol; 5-cyclobutylamino-2-methyl-phenol; 4,5-diamino-1-methyl-1H-pyrazole-3-carbonitrile; 3-methoxy-1-propyl-1H-pyrazole-4,5-diamine; 3-methoxy-1-(2-methoxyethyl)-1H-pyrazole-4,5-diamine; 1-(2-aminoethyl)-3-methoxy-1H-pyrazole-4,5-diamine; 8-methoxy-1,2,4,5-tetrahydropyrazolo[5,1-d][1,3,5]oxadiazepin-9-amine; 1-(2-hydroxyethyl)-3-methoxy-1H-pyrazol-4,5-diamine; 1-cyclohexyl-3-methoxy-1H-pyrazole-4,5-diamine; 6-methoxy-1-methyl-2,3-dihydro-1H-imidazo[1,2-b]pyrazol-7-amine; 2-methoxy-4,5,6,7-tetrahydropyrazolo[1,5-a]pyrimidin-3-amine; 3-methoxy-1-octyl-1H-pyrazole-4,5-diamine; 3-methoxy-1-pentyl-1H-pyrazole-4,5-diamine; 6-methoxy-2,3-dihydro-1H-imidazo[1,2-b]pyrazol-7-amine; 3-methoxy-$N^5,N^5$-dimethyl-1-propyl-1H-pyrazole-4,5-diamine; 1-hexyl-3-methoxy-1H-pyrazole-4,5-diamine; 1-butyl-3-methoxy-1H-pyrazole-4,5-diamine; 1-isopropyl-3-methoxy-1H-pyrazole-4,5-diamine; 1-ethyl-3-methoxy-1H-pyrazole-4,5-diamine; 3-methoxy-1-(4-methoxybenzyl)-1H-pyrazole-4,5-diamine; 3-methoxy-1-(pyridin-2-yl)-1H-pyrazole-4,5-diamine; 1-(4-ethylphenyl)-3-methoxy-1H-pyrazole-4,5-diamine; 3-methoxy-1-p-tolyl-1H-pyrazole-4,5-diamine; 3-cyano-1-(2-hydroxyethyl)-1H-pyrazole-4,5-diamine; 1-butyl-3-cyano-1H-pyrazole-4,5-diamine; 3-cyano-1-phenyl-1H-pyrazole-4,5-diamine; 3-cyano-1-hexyl-1H-pyrazol-4,5-diamine; 1-butyl-3-cyano-1H-pyrazol-4,5-diamine; 3-cyano-1-(4-methoxybenzyl)-

1H-pyrazol-4,5-diamine; 3-cyano-1-isopropyl-1H-pyrazol-4,5-diamine; 1-cyclohexyl-3-fluoro-$N^5$-isopropyl-1H-pyrazole-4,5-diamine; 1-methyl-3-(trifluoromethoxy)-1H-pyrazole-4,5-diamine; 3-fluoro-1-octyl-1H-pyrazole-4,5-diamine; 3-chloro-1-hexyl-1H-pyrazole-4,5-diamine; 3-fluoro-1-(2-hydroxyethyl)-1H-pyrazol-4,5-diamine; 3-chloro-1-(2-hydroxyethyl)-1H-pyrazol-4,5-diamine; 3-chloro-1-(4-hydroxybutyl)-1H-pyrazol-4,5-diamine; 3-chloro-1-(pyridin-2-yl)-1H-pyrazole-4,5-diamine; 3-chloro-1-phenyl-1H-pyrazole-4,5-diamine; 3-chloro-1-ethyl-1H-pyrazole-4,5-diamine; 1-(3-methoxypropyl)-3-(methylsulfinyl)-1H-pyrazole-4,5-diamine; 1-(3-hydroxypropyl)-3-(methylsulfinyl)-1H-pyrazole-4,5-diamine; 1-(4-methoxybenzyl)-3-(methylsulfonyl)-1H-pyrazole-4,5-diamine; 1-methyl-3-(methylsulfonyl)-1H-pyrazole-4,5-diamine; and salts thereof. In some embodiments, developers include but are not limited to: p-phenylenediamine derivatives such as: 2-methyl-benzene-1,4-diamine; benzene-1,4-diamine; 1-(2,5-diamino-phenyl)-ethanol; 2-(2,5-diamino-phenyl)-ethanol; 2-(methoxymethyl)benzene-1,4-diamine; N-(2-methoxyethyl)benzene-1,4-diamine; 2-[(4-amino-phenyl)-(2-hydroxy-ethyl)-amino]-ethanol; 1-(2,5-diaminophenyl)ethane-1,2-diol; 1-(2'-hydroxyethyl)-2,5-diaminobenzene; 1,3-bis(N-(2-hydroxyethyl)-N-(4-amino-phenyl)amino)-2-propanol; 2,2'-[1,2-ethanediyl-bis-(oxy-2,1-ethanediyloxy)]-bis-benzene-1,4-diamine; N,N-bis(2-hydroxyethyl)-p-phenylenediamine; and mixtures thereof; p-aminophenol derivatives such as: 4-amino-phenol; 4-methylamino-phenol; 4-amino-3-methyl-phenol; 4-amino-2-methoxymethyl-phenol; 1-(5-amino-2-hydroxy-phenyl)-ethane-1,2-diol; 4-amino-2-aminomethylphenol; 4-amino-1-hydroxy-2-(2'-hydroxyethylaminomethyl)benzene; 5-aminosalicylic acid and salts thereof; and mixtures thereof; o-phenylenediamine derivatives such as: 3,4-Diaminobenzoic acid and salts thereof; o-aminophenol derivatives such as: 2-amino-phenol; 2-amino-5-methyl-phenol; 2-amino-6-methyl-phenol; N-(4-amino-3-hydroxy-phenyl)-acetamide; 2-amino-4-methyl-phenol; 2-amino-5-ethyl-phenol; and mixtures thereof; and heterocyclic derivatives such as: pyrimidine-2,4,5,6-tetramine; 1-methyl-1H-pyrazole-4,5-diamine; 2-(4,5-diamino-1H-pyrazol-1-yl)ethanol; 1-(4-methylbenzyl)-1H-pyrazole-4,5-diamine; 1-(benzyl)-1H-pyrazole-4,5-diamine; $N^2,N^2$-dimethyl-pyridine-2,5-diamine; 4-Hydroxy-2,5,6-triaminopyrimidine; salts thereof; and mixtures thereof.

In certain embodiments, developers include: 2-methyl-benzene-1,4-diamine; 2-(methoxymethyl)benzene-1,4-diamine; benzene-1,4-diamine; N,N-bis(2-hydroxyethyl)-p-phenylenediamine; 4-amino-phenol; 4-methylamino-phenol; 4-amino-3-methyl-phenol; 2-amino-phenol; 2-amino-5-methyl-phenol; 2-amino-5-ethyl-phenol; 2-amino-6-methyl-phenol; 1-methyl-1H-pyrazole-4,5-diamine; 2-(4,5-diamino-1H-pyrazol-1-yl)ethanol; 2,5-diaminotoluene; 2,5-diaminophenylethyl alcohol; salts thereof; and mixtures thereof.

Couplers

Suitable couplers for use in the compositions described herein include, but are not limited to: phenols, resorcinols, naphthols, m-aminophenols, m-phenylenediamines, and heterocyclic compounds, and derivatives thereof such as: 2-amino-5-ethyl-phenol; naphthalene-1,7-diol; benzene-1,3-diol; 4-chlorobenzene-1,3-diol; naphthalen-1-ol; 2-methyl-naphthalen-1-ol; naphthalene-1,5-diol; naphthalene-2,7-diol; benzene-1,4-diol; 2-methyl-benzene-1,3-diol; 7-amino-4-hydroxy-naphthalene-2-sulfonic acid; 2-isopropyl-5-methylphenol; 1,2,3,4-tetrahydro-naphthalene-1,5-diol; 2-chloro-benzene-1,3-diol; 4-hydroxy-naphthalene-1-sulfonic acid; benzene-1,2,3-triol; naphthalene-2,3-diol; 5-dichloro-2-methylbenzene-1,3-diol; 4,6-dichlorobenzene-1,3-diol; 2,3-dihydroxy-[1,4]naphthoquinone; and 1-Acetoxy-2-methylnaphthalene; m-phenylenediamines such as: 2,4-diaminophenol; benzene-1,3-diamine; 2-(2,4-diaminophenoxy)-ethanol; 2-[(3-amino-phenyl)-(2-hydroxy-ethyl)-amino]-ethanol; 2-methyl-benzene-1,3-diamine; 2-[[2-(2,4-diamino-phenoxy)-ethyl]-(2-hydroxy-ethyl)-amino]-ethanol; 4-{3-[(2,4-diaminophenyl)oxy]propoxy}benzene-1,3-diamine; 2-(2,4-diamino-phenyl)-ethanol; 2-(3-amino-4-methoxy-phenylamino)-ethanol; 4-(2-amino-ethoxy)-benzene-1,3-diamine; (2,4-diamino-phenoxy)-acetic acid; 2-[2,4-diamino-5-(2-hydroxy-ethoxy)-phenoxy]-ethanol; 4-ethoxy-6-methyl-benzene-1,3-diamine; 2-(2,4-diamino-5-methyl-phenoxy)-ethanol; 4,6-dimethoxy-benzene-1,3-diamine; 2-[3-(2-hydroxy-ethylamino)-2-methyl-phenylamino]-ethanol; 3-(2,4-diamino-phenoxy)-propan-1-ol; N-[3-(dimethylamino)phenyl]urea; 4-methoxy-6-methyl-benzene-1,3-diamine; 4-fluoro-6-methylbenzene-1,3-diamine; 2-({3-[(2-hydroxyethyl)amino]-4,6-dimethoxyphenyl}-amino)ethanol; 3-(2,4-diaminophenoxy)-propane-1,2-diol; 2-[2-amino-4-(methylamino)-phenoxy]ethanol; 2-[(5-amino-2-ethoxy-phenyl)-(2-hydroxy-ethyl)-amino]-ethanol; 2-[(3-aminophenyl)amino]ethanol; 2,4-Diamino-5-(2'-hydroxyethyloxy)toluene; N,N-Dimethyl-3-ureidoaniline; N-(2-aminoethyl)benzene-1,3-diamine; 4-{[(2,4-diaminophenyl)oxy]methoxy}-benzene-1,3-diamine; 1-methyl-2,6-bis(2-hydroxyethylamino)benzene; and 2,4-dimethoxybenzene-1,3-diamine; m-aminophenols such as: 3-amino-phenol; 2-(3-hydroxy-4-methyl-phenylamino)-acetamide; 2-(3-hydroxy-phenylamino)-acetamide; 5-amino-2-methyl-phenol; 3-amino-2,6-dimethylphenol; 5-(2-hydroxy-ethylamino)-2-methyl-phenol; 5-amino-2,4-dichloro-phenol; 3-amino-2-methyl-phenol; 3-amino-2,6-dimethyl-phenol; 3-amino-2-chloro-6-methyl-phenol; 5-amino-2-(2-hydroxy-ethoxy)-phenol; 2-chloro-5-(2,2,2-trifluoro-ethylamino)-phenol; 5-amino-4-chloro-2-methyl-phenol; 3-cyclopentylamino-phenol; 5-[(2-hydroxyethyl)amino]-4-methoxy-2-methylphenol; 5-amino-4-methoxy-2-methylphenol; 3-(dimethylamino)phenol; 3-(diethylamino)phenol; 5-amino-4-fluoro-2-methylphenol; 5-amino-4-ethoxy-2-methylphenol; 3-amino-2,4-dichloro-phenol; 3-[(2-methoxyethyl)amino]phenol; 3-[(2-hydroxyethyl)amino]phenol; 5-amino-2-ethyl-phenol; 5-amino-2-methoxyphenol; 5-[(3-hydroxy-propyl)amino]-2-methylphenol; 3-[(3-hydroxy-2-methylphenyl)-amino]propane-1,2-diol; 3-[(2-hydroxy-ethyl)amino]-2-methylphenol; 1-methyl-2-hydroxy-4-(2'-hydroxyethyl)amino-benzene; 1,3-bis-(2,4-diaminophenoxy)propane; and heterocyclic derivatives such as: 3,4-dihydro-2H-1,4-benzoxazin-6-ol; 6-methoxyquinolin-8-amine; 4-methylpyridine-2,6-diol; 2,3-dihydro-1,4-benzodioxin-5-ol; 1,3-benzodioxol-5-ol; 2-(1,3-benzodioxol-5-ylamino)ethanol; 3,4-dimethylpyridine-2,6-diol; 5-chloropyridine-2,3-diol; 2,6-dimethoxypyridine-3,5-diamine; 1,3-benzodioxol-5-amine; 2-{[3,5-diamino-6-(2-hydroxy-ethoxy)-pyridin-2-yl]oxy}-ethanol; 1H-indol-4-ol; 5-amino-2,6-dimethoxypyridin-3-ol; 1H-indole-5,6-diol; 1H-indol-7-ol; 1H-indol-5-ol; 1H-indol-6-ol; 6-bromo-1,3-benzodioxol-5-ol; 2-aminopyridin-3-ol; pyridine-2,6-diamine; 3-[(3,5-diaminopyridin-2-yl)oxy]propane-1,2-diol; 5-[(3,5-diaminopyridin-2-yl)oxy]pentane-1,3-diol; indoline-5,6-diol; 3,5-dimethoxypyridine-2,6-diamine; 6-methoxypyridine-2,3-diamine; 3,4-dihydro-2H-1,4-benzoxazin-6-amine; 4-hydroxy-N-methylindole; 1H-5-methylpyrazol-5-one; 1-phenyl-3-methylpyrazol-5-one; 2,6-dimethylpyrazolo[1,5-b]-1,2,4-triazole; 2,6-dimethyl[3,2-c]-1,2,4-triazole; 6-methylpyrazolo-[1,5-a]benzimidazole; 2,6-dihydroxypyridine; 2,6-dihydroxy-3,4-dimethylpyridine; 5-methylpyrazolo[5,1-e]-1,2,3-triazole; 5-methyl-6-chloropyrazolo[5,1-e]-1,2,3-triazole; 5-phenylpyrazolo[5,1-e]-1,2,3-triazole and its addition salts; 1H-2,6-dimethylpyrazolo[1,5-b]-1,2,4-triazole tosylate; 7,8-dicyano-4-methylimidazolo-[3,2-a]imidazole; 2,7-dimethylpyrazolo[1,5-a]pyrimidin-5-one; 2,5-dimethylpyrazolo[1,5-a]pyrimidin-7-one; and 2-methyl-5-methoxymethyl-pyrazolo[1,5-a]pyrimidin-7-one; 6-hydroxybenzomorpholine; and 3-amino-2-methylamino-6-methoxypyridine; salts thereof; and mixtures thereof.

In some embodiments, couplers include but are not limited to: phenol, resorcinol, and naphthol derivatives such as: 2-amino-5-ethyl-phenol; naphthalene-1,7-diol; benzene-1,3-diol; 4-chlorobenzene-1,3-diol; naphthalen-1-ol; 2-methyl-naphthalen-1-ol; naphthalene-1,5-diol; naphthalene-2,7-diol; benzene-1,4-diol; 2-methyl-benzene-1,3-diol; and 2-isopropyl-5-methylphenol; 1,2,4-trihydroxybenzene; 1-acetoxy-2-methylnaphthalene; and mixtures thereof; m-phenylenediamine derivatives such as: benzene-1,3-diamine; 2-(2,4-diamino-phenoxy)-ethanol; 4-{3-[(2,4-diaminophenyl)oxy]propoxy}benzene-1,3-diamine; 2-(3-amino-4-methoxy-phenylamino)-ethanol; 2-[2,4-diamino-5-(2-hydroxy-ethoxy)-phenoxy]-ethanol; and 3-(2,4-diaminophenoxy)-propan-1-ol; 2,4-diamino-5-(2'-hydroxyethyloxy) toluene; N,N-dimethyl-3-ureidoaniline; 2,4-diamino-5-fluorotoluene; 1-methyl-2,6-bis(2-hydroxyethylamino) benzene; and mixtures thereof; m-aminophenol derivatives such as: 3-aminophenol; 5-amino-2-methyl-phenol; 3-amino-2,6-dimethylphenol; 5-(2-hydroxy-ethylamino)-2-methyl-phenol; and 3-amino-2-methyl-phenol; 1-hydroxy-3-amino-2,4-dichlorobenzene; 1,3-bis-(2,4-diaminophenoxy) propane; 1-hydroxy-2-methyl-5-amino-6-chlorobenzene; 5-Amino-4-chloro-2-methylphenol; and mixtures thereof; and heterocyclic derivatives such as: 3,4-dihydro-2H-1,4-benzoxazin-6-ol; 1,3-benzodioxol-5-ol; 1,3-benzodioxol-5-amine; 1H-indol-4-ol; 1H-indole-5,6-diol; 1H-indol-7-ol; 1H-indol-5-ol; 1H-indol-6-ol; pyridine-2,6-diamine; 2-aminopyridin-3-ol; 4-hydroxy-N-methylindole; 1H-5-methylpyrazol-5-one; 1-phenyl-3-methylpyrazol-5-one; 2,6-dimethylpyrazolo[1,5-b]-1,2,4-triazole; 2,6-dimethyl[3,2-c]-1,2,4-triazole; 6-methylpyrazolo-[1,5-a]benzimidazole; 2,6-dihydroxypyridine; 2,6-dihydroxy-3,4-dimethylpyridine; 6-hydroxybenzomorpholine; 2,6-dihydroxy-3,4-dimethylpyridine; 3,5-diamino-2,6-dimethoxypyridine; 3-amino-2-methylamino-6-methoxypyridine; salts thereof; and mixtures thereof.

In certain embodiments, couplers include: 2-amino-5-ethyl-phenol; benzene-1,3-diol; 4-chlorobenzene-1,3-diol; 4,6-dichlorobenzene-1,3-diol; 2-methyl-benzene-1,3-diol; 2-amino-4-(2'-hydroxyethyl)aminoanisole; 2,4-diaminobenzyl alcohol; 2,4-diaminophenylethyl alcohol; m-phenylenediamine; 5-amino-2-methyl-phenol; 3-amino-2,6-dimethylphenol; 2,4-diaminophenoxyethanol; 4-amino-2-hydroxyphenoxyethanol; 1-naphthol; 2-methyl-naphthol; 3-aminophenol; 3-amino-2-methylphenol; 4-hydroxy-1,2-methylenedioxybenzene; 4-amino-1,2-methylenedioxybenzene; 4-(2'-hydroxyethyl)amino-1,2-methylenedioxybenzene; 1-Methyl-2-hydroxy-4-(2'-hydroxyethyl) aminobenzene; 2,4-diaminophenetole; 2,4-diamino-5-methylphenetole; 4-hydroxyindole; 3-amino-5-hydroxy-2,6-dimethoxypyridine; and 3,5-diamino-2,6-dimethoxypyridine; benzene-1,3-diamine; 2-aminopyridin-3-ol; 1-phenyl-3-methylpyrazol-5-one; salts thereof; and mixtures thereof.

Additionally, in some embodiments, developers and couplers include 5-methoxymethyl-2-aminophenol; 5-ethyl-2-aminophenol; 5-phenyl-2-aminophenol; 5-cyanoethyl-2-aminophenol; salts thereof; and mixtures thereof.

Any of the developers and couplers described above may be combined to form a mixture of developers and couplers. The hair dye compositions of the present invention will generally comprise from about 0.001% to about 10% by weight of the dyeing composition of developer and coupler dyes. For example, compositions providing low intensity dyeing such as natural blond to light brown hair shades generally comprise from about 0.001% to about 5%, in some embodiments, from about 0.1% to about 2%, in certain embodiments, from about 0.2% to about 1% by weight of dyeing composition of developers and couplers. Darker shades such as browns and black typically comprise from 0.001% to about 10% by weight, in some embodiments, from about 0.05% to about 7% by weight, in certain embodiments, from about 1% to about 5% of developers and couplers. Developer compounds are generally used in approximately equimolar quantities with respect to coupler compounds. The developer compound may, however, be present in a greater or lesser quantity with respect to the coupler compound.

Direct Dyes

The inventive compositions may also comprise compatible direct dyes, in an amount sufficient to provide coloring, particularly with regard to intensity. Typically, such an amount will range from about 0.05% to about 4%, by weight of the dye composition. Suitable direct dyes include but are not limited to: Acid Yellow 1; Acid Orange 3; Disperse Red 17; Basic Brown 17; Acid Black 52; Acid Black 1; Disperse Violet 4; 4-nitro-o-phenylenediamine; 2-nitro-p-phenylenediamine; Picramic Acid; HC Red No. 13; 1,4-bis-(2'-hydroxyethyl)-amino-2-nitrobenzene; HC Yellow No. 5; HC Red No. 7; HC Blue No. 2; HC Yellow No. 4; HC Yellow No. 2; HC Orange No. 1; HC Red No. 1; 2-chloro-5-nitro-N-hydroxyethyl-p-phenylenediamine; HC Red No. 3; 4-amino-3-nitrophenol; 2-hydroxyethylamino-5-nitroanisole; 3-nitro-p-hydroxyethylaminophenol; 2-amino-3-nitrophenol; 6-nitro-o-toluidine; 3-methylamino-4-nitrophenoxyethanol; 2-nitro-5-glycerylmethylaniline; HC Yellow No. 11; HC Violet No. 1; HC Orange No. 2; HC Orange No. 3; HC Yellow No. 9; 4-nitrophenyl aminoethylurea; HC Red No. 10; HC Red No. 11; 2-hydroxyethyl picramic acid; HC Blue No. 12; HC Yellow No. 6; hydroxyethyl-2-nitro-p-toluidine; HC Yellow No. 12; HC Blue No. 10; HC Yellow No. 7; HC Yellow No. 10; HC Blue No. 9; N-ethyl-3-nitro PABA; 4-amino-2-nitrophenyl-amine-2'-carboxylic acid; 2-chloro-6-ethylamino-4-nitrophenol; 6-nitro-2,5-pyridinediamine; HC Violet No. 2; 2-amino-6-chloro-4-nitrophenol; 4-hydroxypropylamino-3-nitrophenol; HC Yellow No. 13; 1,2,3,4-tetrahydro-6-nitrochinoxalin; HC Red No. 14; HC Yellow No. 15; HC Yellow No. 14; 3-amino-6-methylamino-2-nitropyridine; 2,6-diamino-3-((pyridine-3-yl)azo)pyridine; Basic Red No. 118; Basic Orange No. 69; N-(2-nitro-4-aminophenyl)-allylamine; 4-[(4-amino-3-methylphenyl)(4-imino-3-methyl-2, 5-cyclohexadien-1-ylidene)methyl]-2-methyl-benzeneamine-hydrochloride; 2-[[4-(dimethyl-amino)phenyl]azo]-1,3-dimethyl-1H-imidazolium chloride; 1-methyl-4-[(methylphenyl-hydrazono)methyl]-pyridinium, methyl sulfate; 2-[(4-aminophenyl)azo]-1,3-dimethyl-1H-imidazolium chloride; Basic Red 22; Basic Red 76; Basic Brown 16; Basic Yellow 57; 7-(2',4'-dimethyl-5'-sulfophenylazo)-5-sulfo-8-hydroxynaphthalene; Acid Orange 7; Acid Red 33; 1-(3'-nitro-5'-sulfo-6'-oxophenylazo)-oxo-naphthalene chromium complex; Acid Yellow 23; Acid Blue 9; Basic Violet 14; Basic Blue 7; Basic Blue 26; sodium salt of mixture of mono-& disulfonic acids (mainly the latter) of quinophthlanone or 2-quinolylindandione; Basic Red 2; Basic Blue 99;

Disperse Red 15; Acid Violet 43; Disperse Violet 1; Acid Blue 62; Pigment Blue 15; Acid Black 132; Basic Yellow 29; Disperse Black 9; 1-(N-methylmorpholinium-propylamino)-4-hydroxy-anthraquinone methylsulfate; HC Blue No. 8; HC Red No. 8; HC Green No. 1; HC Red No. 9; 2-hydroxy-1,4-naphthoquinone; Acid Blue 199; Acid Blue 25; Acid Red 4; Henna Red; Indigo; Cochenille; HC Blue No. 14; Disperse Blue 23; Disperse Blue 3; Disperse Blue 377; Basic Red 51; Basic Orange 31; Basic Yellow 87; and mixtures thereof. Preferred direct dyes include but are not limited to: Disperse Black 9; HC Yellow 2; HC Yellow 4; HC Yellow 15; 4-nitro-o-phenylenediamine; 2-amino-6-chloro-4-nitrophenol; HC Red 3; Disperse Violet 1; HC Blue 2; Disperse Blue 3; Disperse Blue 377; Basic Red 51; Basic Orange 31; Basic Yellow 87; and mixtures thereof.

Surfactants

The compositions according to the present invention may further comprise at least about 0.01% of one or more additional surfactants to those utilised in the gel network thickener system. Surfactants suitable for use herein generally have a lipophilic chain length of from about 8 to about 30 carbon atoms and can be selected from anionic, non-ionic, amphoteric and cationic surfactants and mixtures thereof.

Polymers

The composition of the present invention may optionally further comprise at least about 0.01% of polymer. The polymer can be chosen, for example, from associative polymers, crosslinked acrylic acid homopolymers, and crosslinked copolymers of (meth)acrylic acid and of (C1-C6)alkyl acrylate The polymer may also serve as conditioning agents, as described below. The polymer will generally be used at levels of from about 0.01% to about 20.0% by weight of the composition, preferably of from about 0.1% to about 5%.

Conditioning Agent

The compositions of the present invention may comprise or are used in combination with a composition comprising a conditioning agent. Conditioning agents suitable for use herein are selected from silicone materials, amino silicones, polymeric resins, polyol carboxylic acid esters, cationic surfactants, insoluble oils and oil derived materials and mixtures thereof. Additional materials include mineral oils and other oils such as glycerin and sorbitol.

The conditioning agent will generally be used at levels of from about 0.05% to about 20% by weight of the composition, preferably of from about 0.1% to about 15%, more preferably of from about 0.2% to about 10%, even more preferably of from about 0.2% to about 2%.

Particularly useful conditioning materials are silicones. Silicones can be selected from polyalkylsiloxane oils, linear polydiemthylsiloxane oils containing trimethylsilyl or hydroxydimethylsiloxane endgroups, polymethylphenylsiloxane polydimethylphenylsiloxane or polydimethyldiphenylsiloxane oils, silicone resins, organofunctional siloxanes having in their general structure one or a number of organofunctional group(s), the same or different, attached directly to the siloxane chain. Said organofunctional group(s) are selected from: polyethyleneoxy and/or polypropyleneoxy groups, (per)fluorinated groups, thiol groups, substituted or unsubstituted amino groups, carboxylate groups, hydroxylated groups, alkoxylated groups, quaternium ammonium groups, amphoteric and betain groups. The silicone can either be used as a neat fluid or in the form of an pre-formed emulsion.

Chelants

According to the present invention the compositions may comprise chelants. Chelants are well known in the art and refer to a molecule or a mixture of different molecules each capable of forming a chelate with a metal ion. Chelants are well known in the art and a non-exhaustive list thereof can be found in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996).

Examples of chelants suitable for use herein include EDDS (ethylenediaminedisuccinic acid), carboxylic acids (in particular aminocarboxylic acids), phosphonic acids (in particular aminophosphonic acids) and polyphosphoric acids (in particular linear polyphosphoric acids), their salts and derivatives.

Chelants may be incorporated into the composition of the present invention as stabilizers and or preservatives. In addition it has also been found that chelants provide hair fibre damage benefits and thus they may be utilized in order to further improve the hair damage profile of the present invention. Levels of chelants in the present invention may be as low as about 0.1%, preferably at least about 0.25%, more preferably about 0.5% for the most effective chelants such as diamine-N,N'-dipolyacid and monoamine monoamide-N,N'-dipolyacid chelants (for example EDDS). Less effective chelants will be more preferably used at levels of at least about 1%, even more preferably above about 2% by weight of the composition, depending of the efficiency of the chelant.

Solvents

The composition may further include solvents for use in the compositions such as water, propylene glycol, butoxydigylcol, ethoxydiglycol, hexylene glycol, dipropyleneglycol, glycerol, polyglycerol and mixtures thereof. Typically, the compositions according to the present invention are provided as an aqueous composition. The compositions of the present invention typically comprise from at least about 10%, preferably from about 20%, more preferably from about 30% and most preferably from about 50% by weight of water.

Method of Use

It is understood that the examples of methods of use and embodiments described herein are for illustrative purposes only and that various modifications or changes in light thereof will be suggested to one skilled in the art without departing from the scope of the present invention.

Retail oxidative hair dye compositions are usually sold in kits comprising, in individually packaged components such as separate containers, a dye component (also called "dye cream" for emulsions or "dye liquid" for solutions) comprising the oxidative dye, precursors and alkalizing agent which is typically ammonia in a suitable carrier and; a hydrogen peroxide component (also called "hydrogen peroxide cream" for emulsions or "hydrogen peroxide liquid" for solutions) comprising the oxidizing agent (usually hydrogen peroxide). The consumer mixes the dye component and hydrogen peroxide component together immediately before use and applies it onto the hair.

Similarly, retail bleaching compositions are also usually sold as a kit comprising two or three individually packaged components typically in two or three separate containers. The first component comprises the ammonium ion source (e.g. ammonia), the second component comprises the oxidizing agent and the third (optional) component comprises a second oxidizing agent. The bleaching compositions are obtained by mixing the above-mentioned compositions immediately before use.

For, the professional hair salon market, the hair dye composition and oxidising compositions and or bleaching compositions are typically supplied independently to allow the professional to select a preferred combination.

After working the combined mixture for a few minutes (to insure uniform application to all of the hair), the oxidative dye composition is allowed to remain on the hair for an amount sufficient for the dyeing to take place (usually from about 2 to 60 minutes, typically about 30 to 45 minutes). The consumer or salon professional then rinses the hair thoroughly with water and or shampoo and allows it to dry. It will be observed that the hair has changed from its original colour to the desired colour.

When present in the oxidative dye compositions and bleaching compositions, the optional conditioning agent can be provided in a third container. In the latter case, all three compositions can be mixed immediately before use and applied together, or the content of the third container can be applied (after an optional rinse step) as a post-treatment immediately after the oxidative dye composition or bleaching composition resulting from the mixture of the other containers.

The present invention also includes embodiments wherein the method of colouring or bleaching the hair comprises applying a composition comprising at least one oxidising agent, and a gel network thickening system as defined hereinabove, a cationic polymer and a mica or titanium oxide as defined whereby the composition has a given viscosity and ionic strength.

The kits described hereinabove are well known in the art and the composition in each container can be manufactured utilizing any one of the standard approaches, these include a) 'Oil in water' process, b) 'Phase Inversion' process and c) 'One-pot' process. For example, when using "oil in water" process, surfactants of the present invention are added to approximately 50% of total water amount of the composition at about 90° C., homogenized for 15 to 30 min, then cooled to room temperature thus forming gel network thickener premix; this premix is then mixed cold with remaining amounts of water, other optional components and/or oxidizing agent, thus forming the first and second component parts of the above described bleaching or colouring kit.

The present invention may be utilized in a variety of packaging and dispensing devices. These dispensing devices can come in the form of separate devices which may be used independently or in combination with one another. Typically, the hair colouring or bleaching compositions are contained within separate single or multi compartment containers so that the compositions can be stored separately from one another before use. The compositions are then mixed together by a mixing means and then applied to the consumer's hair by an application means.

The most common packaging device which can be used for the present invention involves storing the developer in a container such as a bottle, tube, aerosol, or a sachet and separately storing the dye lotion in an additional compartment within the developer container or in a separate container which may be identical such as a dual sachet or aerosol systems for example or different such as a bottle and tube system.

The consumer or hair salon professional may mix the developer lotion and the dye lotion by any means. This may simply involve the use of a mixing bowl into which the lotions are dispensed and then mixed, preferably using a mixing means such as a tool. Alternatively it may involve the addition of one of the lotions into the container of the other lotion, (typically the dye lotion is added to the developer lotion), followed by manual shaking or mixing with a tool. Another system involves the perforation or displacement of a seal located between the separate compartments of the dye and developer lotion within a single container or sachet followed by manual mixing within the container or in a separate and or additional container.

The devices described herein above can also be used in combination with a product delivery and or application tool to aid application of the product onto the hair. Again these devices may be of a very simple nature such as a nozzle attached to one of the containers or a separate applicator device such as a comb or brush. Such combs and brushes can be adapted in order to achieve particular effects, whether it be quick and even coverage or root/hairline touch up, or highlights or streaks. Alternatively, the container or one of the containers may be provided with a comb attached to or instead of the dispensing nozzle whereby the product is dispensed through hollow tines and dispensing apertures located in the comb tines. The comb tines may be provided with single or multiple openings along the tines to improve product application and evenness especially root to tip. Product dispensation can be achieved by mechanical pressure applied to the container for example delaminating bottles or any of the mechanisms described hereinabove. The comb may be provided on the container such as to facilitate easy application and may be positioned vertically (so called verticomb) or at an angle to allow the consumer to access all areas. All devices may be designed to have inter-changeability, so that a range of different tools for hair application can be provided to the consumer.

The application devices may also include devices which assist in achieving particular effects such as highlighting such as highlighting combs, brushes and tools, foils and highlighting caps.

Additional device technology can be used to assist in the penetration of the product into the hair. Examples of such technology include heating devices, ultraviolet light devices and ultrasound devices.

Test Methods

Viscosity Test Method

Viscosity measurements are carried out on a controlled stress rheometer of AR500, AR1000 or AR2000 type manufactured by TA Instruments, or equivalent instrument. A 6 cm flat acrylic cross hatched parallel plate geometry (TA item 518600.901) and a stainless steel cross hatched base plate (TA item 570011.001) are used. The rheometer is prepared for flow measurements as per standard manufacturer procedure. The parallel plate geometry gap is set to 1000 microns. The flow procedure is programmed to the rheometer with the following conditions: continuous stress ramp 0.1-300 Pa over 2 minutes at 25° C., including 250 measurement points in linear mode. The final hair colouring mixture is prepare for example by mixing the required parts of the composition in a professional hair stylist's mixing bowl with the professional hair stylist's brush to ensure the even mixed consistency (standard mixing time 1 minute). The product is loaded into the geometry as per standard procedure and the measurement commences at 5 min after the mixture preparation. Shear stress value at 10 $sec^{-1}$ shear rate is obtained from the shear stress vs. shear rate curve, and the corresponding viscosity is calculated by dividing the obtained shear stress by 10.

Root Adhesion Test Method 40 g of the composition mixture is placed in a black plastic bowl at room temperature. The composition is stirred and then pushed with a brush to one side of the bowl. Immediately thereafter, the interface between the composition and the bowl composition is observed by a trained professional stylist and a Root Adhesion index is assigned to the composition as described below:
RA 0=No cracking
RA 1=Short weak cracking, formed within 3 sec
RA 2=Short cracking, formed within 5 sec
RA 3=Long cracking, formed within 10 sec
RA 4=Very long cracking, formed within 15 sec, very good visible, obvious
RA 5=Intensive long crackling, continuing to form after 15 sec.

EXAMPLES

The following examples illustrate hair colouring or bleaching compositions according to the present invention. It is understood that the examples and embodiments described herein are for illustrative purposes only and that various modifications or changes in light thereof will be suggested to one skilled in the art without departing from the scope of the present invention.

The following hair bleaching compositions are prepared which all bleach the hair to an equivalent lift level.

| Ingredient | Comparative Example 1 | Comparative Example 2 | Example 3 | Example 4 | Example 5 | Example 6 |
|---|---|---|---|---|---|---|
| Crodafos ® CES (Cetearyl alcohol, di-cetyl phosphate & ceteth-10 phosphate) | 5 | 4 | 5 | 5 | 4 | 4 |
| Cetearyl alcohol | 1.65 | 2.4 | 1.65 | 1.65 | 2.4 | 2.4 |
| Steareth-200 | 0.5 | 0.625 | 0.25 | 0.5 | 0.375 | 0.625 |
| Ammonia (25%) | 4.095 | 4.095 | 4.095 | 4.095 | 4.095 | 4.095 |
| Propylene glycol | 3 | 3 | 3 | 3 | 3 | 3 |
| Xanthan Gum | 0.04 | 0.04 | 0.04 | 0.04 | 0.04 | 0.04 |
| Polyquaternium 22 | 0 | 0 | 0.25 | 0.25 | 0.25 | 0.25 |
| Mica (Timiron Gleamer MP-45) | 0 | 0 | 0.25 | 0.25 | 0.25 | 0.25 |
| EDTA (tetrasodium salt) | 0.05 | 0.05 | 0.05 | 0.05 | 0.05 | 0.05 |
| Ascorbic Acid | 0.2 | 0.2 | 0.2 | 0.2 | 0.2 | 0.2 |
| Sodium sufite | 0.05 | 0.05 | 0.05 | 0.05 | 0.05 | 0.05 |
| Sodium sulfate | 0.05 | 0 | 0.5 | 0.5 | 0.5 | 0.5 |
| Disodium phosphate | 0.1 | 0.1 | 0.1 | 0.1 | 0.1 | 0.1 |
| Salicylic acid | 0.05 | 0.05 | 0.05 | 0.05 | 0.05 | 0.05 |
| Phosphoric acid | 0.04 | 0.04 | 0.04 | 0.04 | 0.04 | 0.04 |
| EDDS (trisodium salt) | 1 | 1 | 0.5 | 0.5 | 0.5 | 0.5 |
| Sodium lauryl sulfate | 0.1 | 0.1 | 0.1 | 0.1 | 0.1 | 0.1 |
| Perfume | 0.125 | 0.125 | 0.125 | 0.125 | 0.125 | 0.125 |
| Polyvinylpyrrolidone/Styrene Copolymer | 1.65 | 1.65 | 1.65 | 1.65 | 1.65 | 1.65 |
| Hydrogen peroxide (35%) | 12.855 | 12.855 | 12.855 | 12.855 | 12.855 | 12.855 |
| Water qs | qs | qs | qs | qs | qs | qs |

The viscosity and root adhesion for the comparative and exemplified compositions was determined using the test method described herein above and the results are given below. Root adhesion values of 0 and 1 are considered acceptable. Examples 1 and 2 are representative of the prior art and exhibit poor root adhesion.

| | example | | | | | |
|---|---|---|---|---|---|---|
| Composition | 1 | 2 | 3 | 4 | 5 | 6 |
| Viscosity Pas | 12.08 | 12.49 | 12.87, | 15.25 | 12.73 | 14.66 |
| Root adhesion index | 4 | 4 | 1 | 0 | 0 | 0 |
| Ionic strength mole/kg | 0.195 | 0.195 | 0.215 | 0.215 | 0.215 | 0.215 |

The formulation examples 7 to 10 below were also prepared in order to demonstrate the single variable affect of the components of the invention.

| Ingredient | Example 7 | Example 8 | Example 9 | Example 10 |
|---|---|---|---|---|
| Crodafos ® CES (Cetearyl alcohol, di-cetyl phosphate & ceteth-10 phosphate | 5 | 5 | 5 | 5 |
| Cetearyl alcohol | 1.65 | 1.65 | 1.65 | 1.65 |
| Steareth-200 | 0.5 | 0.5 | 0.5 | 0.5 |
| Ammonia (25%) | 4.095 | 4.095 | 4.095 | 4.095 |
| Propylene glycol | 3 | 3 | 3 | 3 |
| Xanthan Gum | 0.04 | 0.04 | 0.04 | 0.04 |
| Polyquaternium 22 | 0 | 0.25 | 0 | 0.25 |
| Mica (Timiron Gleamer MP-45) | 0 | 0 | 0.25 | 0.25 |
| EDTA (tetrasodium salt) | 0.05 | 0.05 | 0.05 | 0.05 |
| Ascorbic Acid | 0.2 | 0.2 | 0.2 | 0.2 |
| Sodium sufite | 0.05 | 0.05 | 0.05 | 0.05 |

-continued

| Ingredient | Example 7 | Example 8 | Example 9 | Example 10 |
|---|---|---|---|---|
| Sodium sulfate | 0 | 0 | 0 | 0 |
| Disodium phosphate | 0.1 | 0.1 | 0.1 | 0.1 |
| Salicylic acid | 0.05 | 0.05 | 0.05 | 0.05 |
| Phosphoric acid | 0.04 | 0.04 | 0.04 | 0.04 |
| EDDS (trisodium salt) | 1 | 1 | 1 | 1 |
| Sodium lauryl sulfate | 0.1 | 0.1 | 0.1 | 0.1 |
| Perfume | 0.125 | 0.125 | 0.125 | 0.125 |
| Polyvinylpyrrolidone/Styrene Copolymer | 1.65 | 1.65 | 1.65 | 1.65 |
| Hydrogen peroxide 35% | 12.855 | 12.855 | 12.855 | 12.855 |
| Water qs | qs | qs | qs | qs |

Example 7 is the comparative example, examples 8 and 9 which are not representative of the present invention will not exhibit satisfactory root adhesion, whereas example 10 which is representative of the present invention will exhibit root adhesion. The ionic strength of the example compositions 7 to 12 is 0.4 mole/kg.

PRIOR ART COMPARATIVE EXAMPLES

Example 1 from EP1832273A was prepared according to the instructions therein and mixed with the developer formulations 11 and 12. The ionic strength and viscosity of the resultant mixtures was determined according to the test method described hereinabove. The ionic strength for both formulations was 0.95 mol/kg and the viscosity was 3.3 Pas (Example 1 & developer 11) and 7.6 Pas (Example 1 & developer 12) respectively. Such formulations thus have a viscosity value which is typical for retail applications and which will also not exhibit root adhesion problems.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair colouring or bleaching composition comprising an oxidizing agent, a gel network thickening system comprising:
   i) a first surfactant component selected from the group consisting of C14 to 30 alkyl phosphate, C14 to C30 alkyl ether phosphate and mixtures thereof,
   ii) a second component selected from C14 to C30 fatty alcohols; and
   iii) a third surfactant component selected from polyoxyethylene C14 to C30 alkyl ethers; wherein said composition comprises at least 1% of said first surfactant and at least 3% of the sum of said first surfactant component, second component and third surfactant component, wherein said composition further comprises at least 0.2% of mica, titanium oxide or a mixture thereof, at least 0.2% of a cationic polymer, wherein said composition has an ionic strength of less than 0.75 mole/kg and a viscosity of from about 9 Pa·s to about 16 Pa·s.

2. A hair colouring or bleaching composition according to claim 1, wherein said cationic polymer is selected from the group consisting of polyquaternium 7, polyquaternium 22, polyquaternium 37, polyquaternium 87 and mixtures thereof.

3. A hair colouring or bleaching composition according to claim 1, wherein said composition comprises from about 0.5 to about 1.5% of mica, titanium oxide or a mixture thereof.

4. A hair colouring or bleaching composition according to claim 1, wherein said composition comprises from about 0.5% to about 1.5% of said cationic polymer.

5. A hair colouring or bleaching composition according to claim 1, wherein said composition comprises from about 1 to about 3% of said first surfactant component, from about 2 to about 8% of said second component and from about 0.1 to about 5% of said third surfactant component.

6. A hair colouring or bleaching composition according to claim 1, wherein said ionic strength is from about 0.1 to less than about 0.75 mole/kg.

7. A hair colouring or bleaching composition according to claim 1, wherein said ionic strength is from about 0.2 to about 0.6 mole/kg.

8. A hair colouring or bleaching composition according to claim 1, wherein said composition further comprises at least one source of alkalizing agent.

9. A hair colouring or bleaching composition according to claim 8 wherein the alkalizing agent is a source of ammonium ions or ammonia.

10. A hair colouring or bleaching composition according to claim 1, wherein said third surfactant is selected from polyoxyethylene C14 to C30 alkyl ethers having at least 25 ethylene oxide units.

11. A hair colouring or bleaching composition according to claim 10, wherein said third surfactant is selected from polyoxyethylene C14 to C30 alkyl ethers having from about 100 to about 200 ethylene oxide units.

12. A hair colouring composition according to claim 1, wherein said composition further comprises at least one dye component selected from an oxidative dye precursor or a pre-formed dye.

13. A method of treating hair comprising the steps of applying the composition according to claim 1 to the hair, leaving said composition on the hair for from about 2 to about 60 minutes and subsequently rinsing said composition from the hair.

* * * * *